Figure 1:
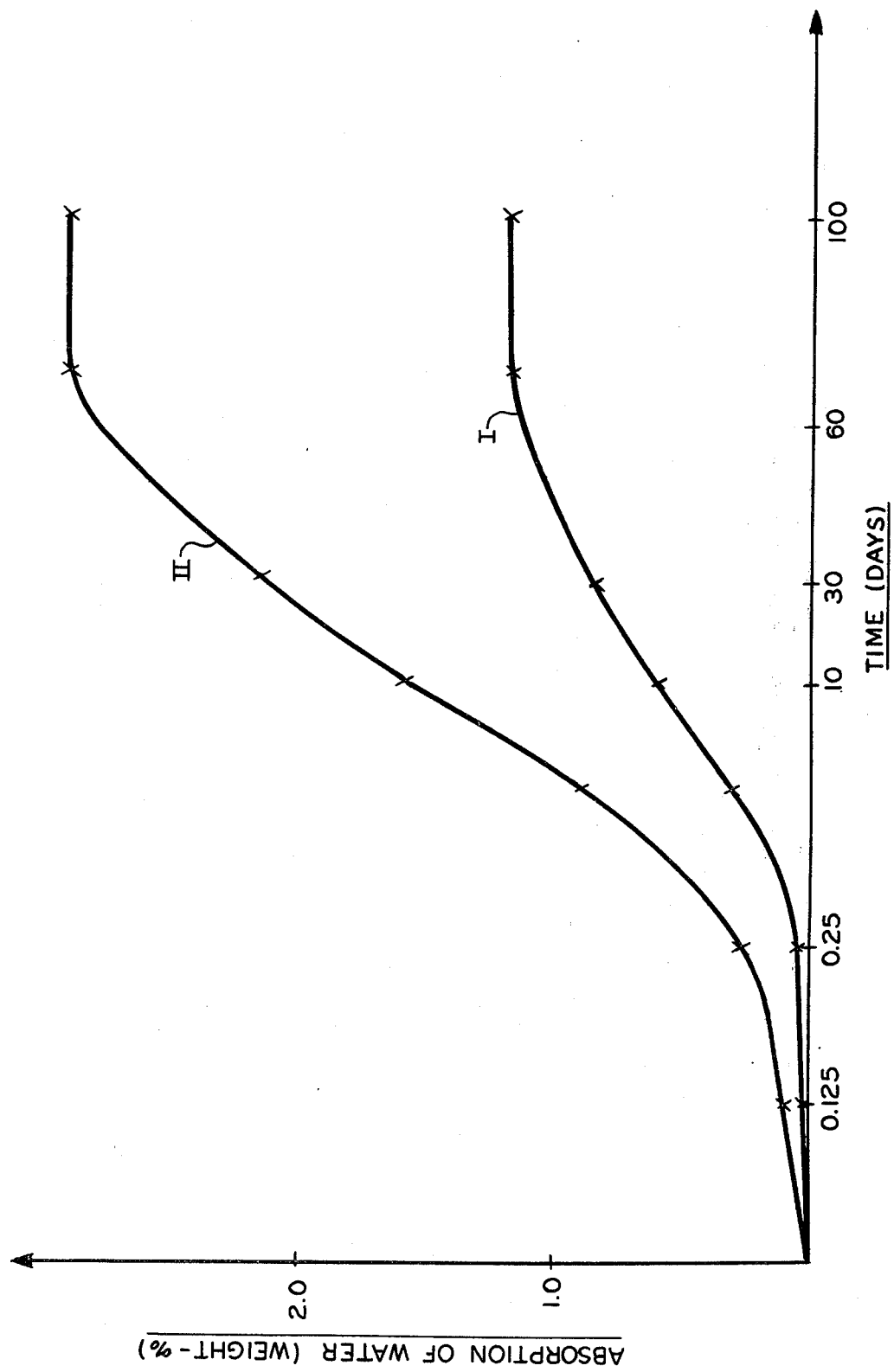

United States Patent

Gross et al.

[11] 4,002,669
[45] Jan. 11, 1977

[54] HYDROXY GROUP CONTAINING DIESTERS OF ACRYLIC ACID

[75] Inventors: Albert Gross, Frankfurt am Main; Roland Schaefer, Friedrichsdorf, Taunus, both of Germany

[73] Assignee: Kulzer & Co. GmbH, Bad Homberg vor der Hohe, Germany

[22] Filed: Jan. 27, 1975

[21] Appl. No.: 544,532

[30] Foreign Application Priority Data

Feb. 12, 1974 Germany .................... 2406557

[52] U.S. Cl. .................... 260/486 B; 106/35; 526/321; 526/273
[51] Int. Cl.[2] .................... C07C 69/54
[58] Field of Search ............ 260/486 R, 486 B

[56] References Cited

UNITED STATES PATENTS 3,810,938  5/1924  Schmitt et al. ............ 260/486 R

FOREIGN PATENTS OR APPLICATIONS 657,894  2/1963  Canada .................... 260/486 R Primary Examiner—Paul J. Killos
Attorney, Agent, or Firm—Burgess, Dinklage & Sprung

[57] ABSTRACT

Polymerizable hydroxy-group-containing diesters of acrylic acids for dental material are prepared by reacting 3-(3,4-epoxycyclohexyl)-8,9-epoxy-2,4-dioxaspiro(5,5) undecane or a bis-epoxide of formula (A)

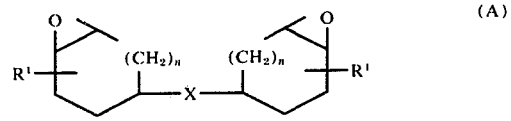

or a bis-epoxide of formula (B)

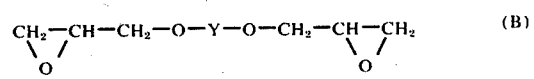

with a hydroxyalkylacrylate or hydroxyalkylmethacrylate containing 2 to 10 carbon atoms in the alkyl portion, $n$ being 0 or 1 in formula (A) with the proviso that when $n$ is 0,
X is —O— and
$R^1$ is —H; and when $n$ is 1,
X is selected from the group of alkylene with 1 to 10 carbon atoms, $C_{1-3}$-alkyl substituted alkylene with 1 to 10 carbon atoms, —O—$(CH_2)_m$—O— where $m$ is 1 to 10, —$CH_2$—OCO—$(CH_2)_p$—COO—$CH_2$ where $p$ is 1 to 6, and —$CH_2$—OCO—, and
$R^1$ is —H or —$CH_3$, and in formula (B)

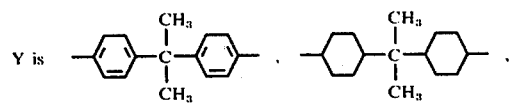

or tricyclo-[5.2.1.0[2,6]]-decylene.

8 Claims, 2 Drawing Figures

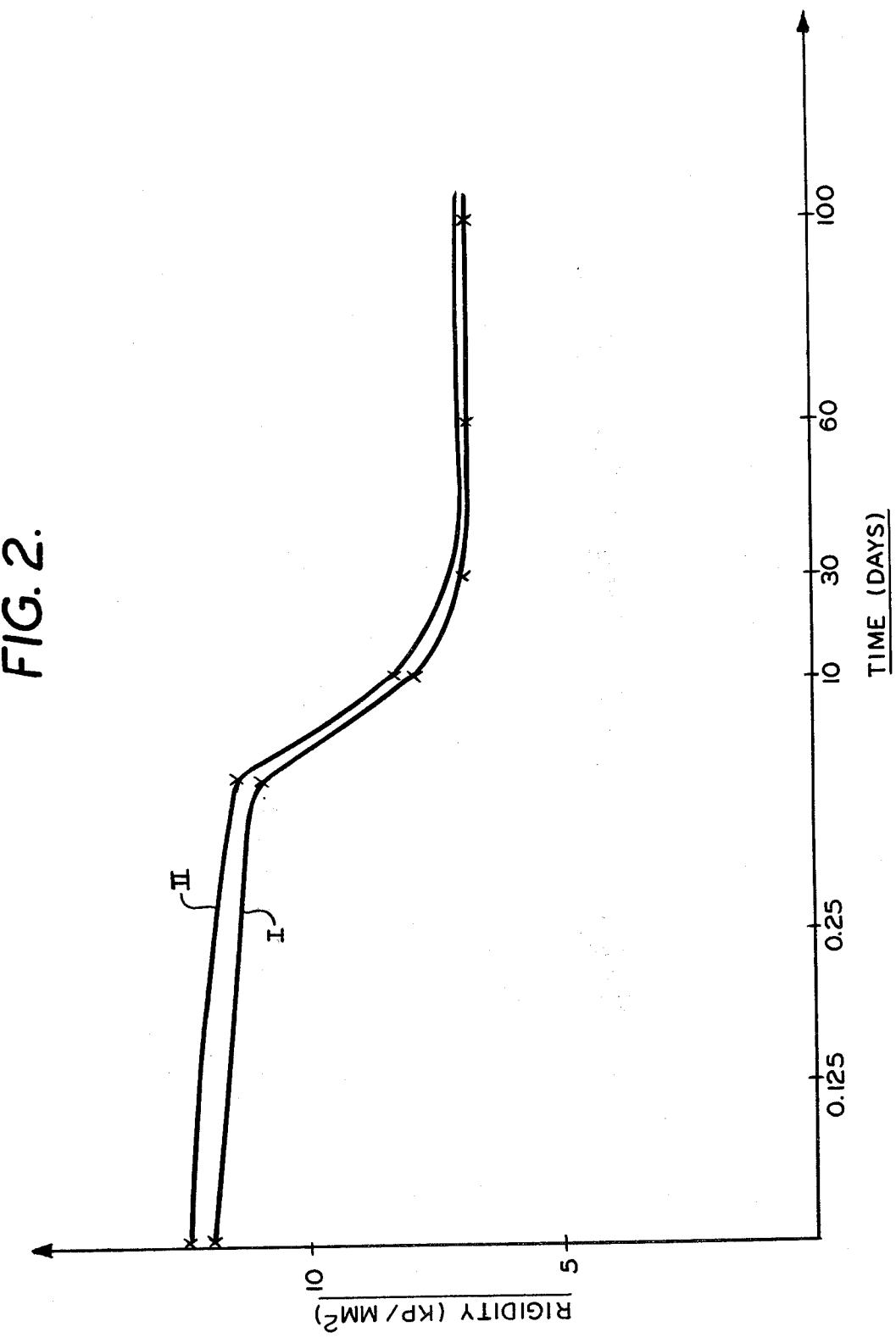

HYDROXY GROUP CONTAINING DIESTERS OF ACRYLIC ACID

BACKGROUND

The invention relates to hydroxy group-containing diesters of acrylic acids, especially dimethacrylates, and their use in dental material, especially in tooth filling material.

Tooth filling materials made of plastics have been known for many years. The first of these materials consisted of mixtures of monomeric and polymeric methylmethacrylate which, upon the addition of a catalyst or of a system consisting of catalyst and accelerator, hardened within a few minutes under the temperature conditions prevailing within the mouth.

An improvement of the mechanical characteristics of these filling materials was achieved by the addition of finely divided fillers such as quartz or aluminum silicates, and an improvement of the aesthetic effect was achieved by the development of new catalyst systems which cause no discoloration.

Tooth filling materials must harden within a reasonable time, must be biologically compatible, and must provide fillings having good strength characteristics. One special problem is the shrinkage of the material which occurs during polymerization. This results in the development of a shrinkage gap or marginal gap between the wall of the tooth cavity and the filling, which greatly accelerates the development of secondary caries.

Through the development of filling materials known as "composites," which are composed of a finely divided inorganic filler treated with a silane to improve adhesion between the filler particles and the plastic, a polymerizable monomeric compound as binding agent, a catalyst and, in some cases, accelerators and other additives such as pigments, for example, the plastic-based tooth filling materials have been so improved that they are in no way inferior in importance to the silicate cements, and in some ways are even more appropriate than the latter, especially for visible fillings in the front teeth.

The first of these new materials was developed by Rafael L. Bowen and is described in U.S. Pat. No. 3,066,112. It contains as the monomeric binding agent a diacrylate or dimethacrylate containing hydroxy groups which is prepared by the reaction of a bisphenol with glycidyl acrylate or glycidyl methacrylate. The reaction product formed by bisphenol A and glycidyl methacrylate, known as bis-GMA, is considered to be especially suitable. It is contained in a number of commercial products as a monomeric binding agent. Dental fillings made therewith have good mechanical strength. The high viscosity of the monomeric binding agents, however, makes them difficult to handle.

Esters of acrylic acids having a low viscosity, which are suitable for use in dental filling materials, are known from U.S. Pat. No. 3,730,947. These are especially 1,3-bis-(2-hydroxy-3-acryloyloxypropoxy)-benzene and the corresponding methacryloyloxy derivative.

These compounds do have a lower viscosity than bis-GMA, which facilitates handling them, but their lower molecular weight produces a greater shrinkage in polymerization and consequently a greater amount of shrinkage gaps or marginal gaps.

THE INVENTION

It is the object of the invention to find hydroxy group-containing diesters of acrylic acids, especially dimethacrylates, which will permit easy handling and a minimum of shrinkage in polymerization, and with which a minimum marginal gap will be achieved in completed dental fillings.

The acrylic acid diesters containing polymerizable hydroxy groups, especially dimethacrylates, which are prepared by the reaction of a bis-epoxide with another reactant, are characterized in accordance with the invention by the fact that they are prepared by the reaction of 3-(3,4-epoxycyclohexyl)-8,9-epoxy-2,4-dioxaspiro-(5,5)-undecane, or of a bis-epoxide of the general formula

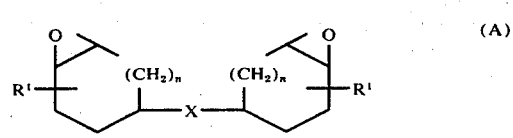

or of a bis-epoxide of the general formula

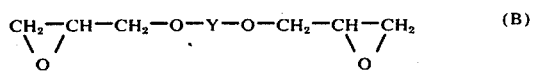

with a hydroxyalkylacrylate or hydroxyalkylmethacrylate containing 2 to 10 carbon atoms in the alkyl radical, $n$ in General Formula A being equal to 0 or 1, but if $n = 0$
$X = -O-$
$R^1 = -H$ and if
$n = 1$,
$X =$ an alkylene radical of 1 to 10 C atoms, a $C_{1-3}$ alkyl-substituted alkylene radical of 1 to 10 C atoms, $-O-(CH_2)_m-O-$ in which $m = 1-10$, $-CH_2-OCO-(CH_2)_p-COO-CH_2-$ in which $p = 1-6$, and $-CH_2-OCO-$, and
$R^1 = -H$ or $-CH_3$ and, in General Formula B,

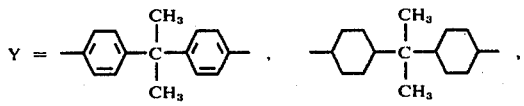

or a tricyclo-[5.2.1.0$^{2,6}$]-decyclene radical.

The following have proven useful as bis-epoxides corresponding to General Formula A: bis-(2,3-epoxycyclopentyl)-ether, 2,2-bis-(3,4-epoxycyclohexyl)-propane, 1,2-bis-(3,4-epoxycyclohexoxy)-ethane, bis-(3,4-epoxy-6-methylcyclohexylmethyl)-adipate, and 3,4-epoxycyclohexanecarboxylicacid-3',4'epoxycyclohexylmethylester.

The following have proven useful as bis-epoxides corresponding to General Formula B: bisphenol-A-diglycidylether and the diglycidyl ether of dihydroxy-tricyclo-[5.2.1.0$^{2,6}$]-decane The following have proven useful as hydroxyalkyl acrylates and methacrylates: 2-hydroxyethylacrylate, 2-hydroxypropylacrylate, 2-hydroxyethylmethacrylate and 2-hydroxypropylmethacrylate.

The diacrylates and dimethacrylates of the invention advantageously combine the characteristics of lesser shrinkage in polymerization and of a viscosity making them easier to handle. Their use as monomeric binding agents in dental filling materials of the composite type results in fillings having good mechanical strength characteristics.

The finely divided filler materials can be quartz, aluminum oxide, lithium aluminum silicates or other inorganic materials commonly used for this purpose, which have been treated with a silane, such as trimethoxy-(3-methacryloyloxypropyl)-silane, for example, to improve adhesion to the plastic.

Dental materials containing diacrylates and dimethacrylates in accordance with the invention, plus amorphous, preferably silanized silica with a maximum particle size of 0.07 micrometers as filler, have proven particularly valuable. The term, "amorphous silica," as used herein, refers to precipitated silica, or silica prepared by flame hydrolysis, which can also contain up to 20% aluminum oxide by weight. The filler content amounts to from 30 to 80% by weight.

Setting is accomplished in the presence of known redox systems composed of organic peroxy compounds and barbituric acid derivatives plus small amounts of copper salts or copper complex compounds and chlorine in inorganic form as co-catalysts, or of organic peroxy compounds and amines as catalysts. Examples of suitable peroxy compounds are tert.-butyl hydroperoxide, and tert.-butyl perbenzoate; examples of barbituric acid derivatives are 1,3,5-trimethyl, 1-benzyl-5-phenyl and 5-butyl barbituric acid; and examples of amines are N,N-dimethyl-p-toluidine and N,N-bis-(hydroxyethyl)-p-toluidine. The preparation of the diacrylates and dimethacrylates in accordance with the invention from bis-1,2-epoxides and hydroxyalkyl acrylates and methacrylates, which is described in the following examples, is performed by the method described in Houben-Weyl, "Methoden der organischen Chemie", 4th ed., vol. 6/3, 1965, pp. 40 sqq., for the addition of alcohols onto 1,2-epoxides. The reaction temperature, however, should not exceed 120° C, in order to prevent premature polymerization.

The starting products and the boron trifluoride etherate used as catalyst are distilled prior to the performance of the reactions.

EXAMPLES

EXAMPLE 1 — Reaction of 3,4-epoxycyclohexanecarboxylic-acid-3′4′-epoxycyclohexylmethylester with 2-hydroxyethylmethacrylate To 120 g (0.92 mole) of 2-hydroxyethylmethacrylate, stabilized with 700 ppm of 2,6-di-tert.-butyl-4-methylphenol, and 0.25 ml of $BF_3$-etherate, 100 g (0.40 mole) of 3,4-epoxycyclohexanecarboxylicacid-3′,4′-epoxycyclohexylmethylester is stirred in, drop by drop, the internal temperature of the reaction flask being maintained at approximately 15° C. After such addition has been completed, 10 g (0.08 mole) of 2-hydroxyethylmethacrylate, in which 0.15 ml of $BF_3$-etherate is dissolved, is also added. Then the reaction mixture is let stand for 5 hours at room temperature. It is then dissolved by adding benzene, and washed neutral successively with water, with 5% aqueous NaOH solution, and again with water. After removal of the benzene on the rotatory evaporator, the unreacted 2-hydroxyethylmethacrylate is removed by distillation in vacuo (1.5 mm) at 70° to 80° C. The yield of dimethacrylate, a water-clear, viscous liquid, amounts to approximately 80%.

EXAMPLE 2 — Reaction of bis-(3,4-epoxy-6-methylcyclohexylmethyl)-adipate with 2-hydroxyethylmethacrylate To 0.92 mole of 2-hydroxyethylmethacrylate, stabilized with 700 ppm of 2,6-di-tert.-butyl-4-methylphenol, and 0.25 ml of $BF_3$-etherate, 0.40 mole of bis-(3,4-epoxy-6-methylcyclohexylmethyl)-adipate is added drop by drop, with stirring, the internal temperature of the reaction flask being maintained at about 15° C. After such addition has been completed, 0.08 mole of 2-hydroxyethylmethacrylate containing 0.15 ml of $BF_3$-etherate dissolved in it is added. The reaction mixture, after standing for 5 hours at room temperature, is then processed the same as in Example 1. The yield of dimethacrylate is 80%.

EXAMPLE 3 — Reaction of 3-(3,4-epoxycyclohexyl)-8,9-epoxy-2,4-dioxaspiro-(5,5)-undecane with 2-hydroxyethylmethacrylate To 0.92 mole of 2-hydroxyethylmethacrylate, stabilized with 700 ppm of 2,6-di-tert.-butyl-4-methylphenol, and 0.25 ml of $BF_3$-etherate, 0.40 mole of 3-(3,4-epoxycyclohexyl)-8,9-epoxy-2,4-dioxaspiro-(5,5)-undecane is added drop by drop with stirring, the internal temperature of the reaction flask being maintained at about 15° C.

After such addition is completed, 0.08 mole of 2-hydroxyethylmethacrylate in which 0.15 ml of $BF_3$-etherate is dissolved is also added. After the reaction mixture thus obtained has stood for 5 hours, it is processed as described in Example 1. The dimethacrylate yield is 85%.

EXAMPLE 4 — Reaction of bis-(2,3-epoxycyclopentyl)-ether with 2-hydroxyethylmethacrylate To 92 g (0.75 mole) of 2-hydroxyethylmethacrylate, stabilized with 700 ppm of 2,6-di-tert.-butyl-4-methylphenol, and 0.18 ml of $BF_3$-etherate, 54 g (0.28 mole) of bis-(2,3-epoxycyclopentyl)-ether is added drop by drop, with stirring, over a period of 5 hours, the internal temperature being maintained at 25° C. After such addition has been completed, 0.12 ml of $BF_3$-etherate is added. The reaction mixture obtained is let stand for 3 hours at room temperature, then dissolved with benzene and washed neutral successively with water, 5% aqueous NaOH solution, and water. The benzene is removed on the rotatory evaporator and then the unreacted 2-hydroxyethylmethacrylate is removed by distillation in vacuo (1.5 mm) at 70° to 80° C. A liquid is obtained in an 85% yield whose principal component is dimethacrylate. The saponification number is 5% higher than the theoretical value calculated for the dimethacrylate.

EXAMPLE 5 — Reaction of the bis-glycidyl ether of dihydroxytricyclo-[5.2.1.0$^{2,6}$]-decane with 2-hydroxyethylmethacrylate To 0.72 mole of 2-hydroxyethylmethacrylate, stabilized with 770 ppm of 2,6-di-tert.-butyl-4-methylphenol, and 0.18 ml of $BF_3$-etherate, 0.28 mole of the bis-glycidyl ether of dihydroxytricyclo-[5.2.1.0$^{2,6}$]-decane was added drop by drop, over a period of 5 hours, with stirring, at an internal temperature of 25° C. Upon completion of this addition, another 0.12 ml of BF$_3$-etherate was added. The reaction mixture thus obtained was processed as described in Example 1 after 3 hours of standing at room temperature. The reaction product obtained in an 85% yield had a saponification number that was 10% below the theoretical value calculated for the dimethacrylate.

EXAMPLE 6 — Reaction of bisphenol-A-diglycidyl ether with 2-hydroxyethylmethacrylate To 0.72 mole of 2-hydroxyethylmethacrylate, stabilized with 700 ppm of 2,6-di-tert.-butyl-4-methylphenol, and 0.18 ml of BF$_3$-etherate, 0.28 mole of bisphenol-A-diglycidyl ether was added drop by drop, with stirring, at an internal temperature of 25° C, over a period of 5 hours. After such addition was completed, another 0.12 ml of BF$_3$-etherate was added. After standing for 3 hours at room temperature, the reaction mixture was processed as described in Example 1. The reaction product obtained in an 80% yield had a saponification number that was 15% lower than the theoretical value for the dimethacrylate.

EXAMPLE 7 — Reaction of 3,4-epoxycyclohexanecarboxylicacid-3',4'-epoxycyclohexylmethylester with 2-hydroxypropylmethacrylate To 0.92 mole of 2-hydroxypropylmethacrylate, stabilized with 700 ppm of 2,6-di-tert.-butyl-4-methylphenol, and 0.25 ml of BF$_3$-etherate, 0.40 mole of 3,4-epoxycyclohexanecarboxylicacid-3',4'-epoxycyclohexylmethylester was added drop by drop, with stirring, at an internal temperature of 15° C. When this addition was completed, another 0.08 mole of 2-hydroxypropylmethacrylate in which 0.15 ml of BF$_3$-etherate was dissolved, was added. The reaction mixture thus obtained was dissolved with benzene after standing for 5 hours at room temperature, and washed neutral, first with water, then with 5% aqueous NaOH solution, and finally with water. After removal of the benzene in a rotatory evaporator, the excess 2-hydroxypropylmethacrylate was removed by distillation in vacuo (1.5 mm) at 70° to 80° C. The dimethacrylate was obtained in a 100% yield. Its saponification number was the same as the calculated theoretical value.

EXAMPLE 8 — Reaction of 3,4-epoxycyclohexanecarboxylicacid-3',4'-epoxycyclohexylmethylester with 2-hydroxyethylacrylate To 106 g (0.92 mole) of 2-hydroxyethylacrylate, stabilized with 700 ppm of 2,6-di-tert.-butyl-4-methylphenol, and 0.25 ml of BF$_3$-etherate, 100 g (0.40 mole) of 3,4-epoxycyclohexanecarboxylicacid-3',4'-epoxycyclohexylmethylester was added drop by drop, with stirring, the internal temperature of the reaction flask being maintained at approximately 15° C. After the completion of this addition another 9.3 g (0.08 mole) of 2-hydroxyethylacrylate, in which 0.15 ml of BF$_3$-etherate was dissolved, was added. Then the reaction mixture was let stand for 5 hours at room temperature. Then it was dissolved with benzene and washed neutral successively with water, with 5% aqueous NaOH solution, and then again with water. After removal of the benzene in the rotary evaporator, the unreacted 2-hydroxyethylacrylate was removed by distillation in vacuo (1.5 mm) at 70° to 80° C. The yield of diacrylate, a water-clear, viscous liquid, amounted to about 80%.

For the determination of the strength characteristics of the test specimens prepared using the above-described diacrylates and dimethacrylates as monomeric binding agents, a dental filling material of the composite type was prepared by mixing together a powder containing inorganic filler and barbituric acid derivatives as the first component of the catalyst, a liquid containing diacrylate or dimethacrylate, as the case may be, and a second component of the catalyst system consisting of peroxy compounds. 3,4-dimethylpyrazolone-(5) can be added to the powder, or α-methylstyrene can be added to the liquid, to serve as a polymerization retarder. In the following Example 9 is described the composition of the individual components of the composite material and the manner in which the latter is processed.

EXAMPLE 9 a. Powder with 1st component of catalyst:

98.5 wt.-% glass particles treated with trimethoxy-(3-methacryloyloxy-propyl)-silane, particle size under 60μ.
0.5 wt.-% 1-benzyl-5-phenylbarbituric acid
0.5 wt.-% 5-butylbarbituric acid
0.4 wt.-% 3,4-dimethylpyrazolone-(5)
0.3 wt.-% paraffin, melting point 48° C.

b. Liquid:

80.0 wt.-% diacrylate or dimethacrylate,
20.0 wt.-% methacrylic acid methyl ester
0.01 wt.-% copper naphthenate c. 2nd component of catalyst:

10.0 wt.-% tert.-butylhydroperoxide
10.0 wt.-% tert.-butylperbenzoate
1.0 wt.-% β-phenylethyldibutylammoniumaceticacidethylesterchloride
79.0 wt.-% dioctylphthalate Four grams of powder, 1 g of liquid and 0.1 ml of the 2nd catalyst component are mixed together. The working time amounts to 1 minute, the setting time to about 5 minutes.

After the test specimens obtained by the use of the dimethacrylates described in Examples 1 to 7 and of the diacrylate described in Example 8 have set, their bending strength was determined in accordance with the ISO draft standard for plastic dental filling materials (Document No. ISO/TC 106/WG 1/109, April 1973), and their Rockwell B hardness was determined pursuant to DIN 50103. The values measured are given in the Table, in which the composite materials prepared using the diesters described in Examples 1 to 8 are identified with the numerals I to VIII. The Table contains the values of test specimens prepared from dental filling materials obtainable on the market, for purposes of comparison.

TABLE

| Composite material | Bending Strength (kp/mm²) | Rockwell B hardness |
| --- | --- | --- |
| I | 12.5 | 105 |
| II | 10.0 | 90 |
| III | 9.5 | 90 |
| IV | 13.8 | 103 |
| V | 10.5 | 95 |

TABLE-continued

| Composite material | Bending Strength (kp/mm²) | Rockwell B hardness |
|---|---|---|
| VI | 10.7 | 100 |
| VII | 9.0 | 90 |
| VIII | 11.3 | 102 |
| SMILE (commercially available products) | 14.4 | 104 |
| ADAPTIC (commercially available products) | 10.1 | 106 |
| HL-72 (commercially available products) | 11.5 | 106 |

As the Table shows, Composite Material I has a bending strength of 12.5 kp/mm² and a Rockwell B hardness of 105, and thus its strength characteristics are equal to those of the composite dental filling materials that are on the market.

Hitherto there has been an effort to develop plastic-base dental filling materials which will alter as little as possible after setting in the mouth. The moisture absorption taking place in the ever moist atmosphere of the mouth should be as little as possible, since it adversely affects the mechanical strength of the fillings.

Test specimens made with the use of the dimethacrylate described in Example 1 in accordance with the invention behave differently than those made from known dental filling materials with regard to moisture absorption and the effect of moisture absorption on strength.

Moisture Absorption

To determine the moisture absorption of specimens prepared from Composite Material I, the specimens are stored in water at a temperature of 37° C. For comparison, the moisture absorption of specimens made from a composite material based on bis-GMA is tested in the same manner.

The increase in the weight of the specimens due to the absorption of water, as measured in the experiments, is plotted graphically in the appended FIG. 1 in relation to the time of storage in water. Curve I shows the moisture absorption of a specimen based on bis-GMA, and Curve II shows that of a specimen on the basis of the dimethacrylate of Example 1 of the invention, referred to as CDM.

The moisture absorption of the CDM-base material takes place more rapidly and is greater than that of the material on the basis of bis-GMA. Thus, when CDM is used in a dental filling material, a more rapid and complete closing is achieved of the marginal gap caused by shrinkage during polymerization. A permanent marginal seal is assured by the always moist ambient of the dental filling within the mouth.

Effect of Moisture Absorption on Bending Strength

To study the effect of moisture absorption on bending strength, test specimens prepared both from bis-GMA materials and from CDM-based materials were stored in water at 37° C and their bending strength was determined in accordance with the ISO draft standard for plastic dental filling materials (Document No. ISO/TC 106/WG 1/109, April 1973).

The values obtained for the bending strength are plotted graphically in the appended FIG. 2 in relation to the time of storage in water. Curve I shows the bending strength of a test specimen made from material based on bis-GMA, and Curve II represents that of a specimen made from material based on CDM. As the curves indicate, the CDM material has just as good strength as the material based on bis-GMA in spite of the greater moisture absorption.

What is claimed is:

1. Polymerizable hydroxy-group-containing diesters of acrylic acids prepared by the reacting 3-(3,4-epoxycyclohexyl)-8,9-epoxy-2,4-dioxaspiro(5,5)undecane or a bis-epoxide of formula (A)

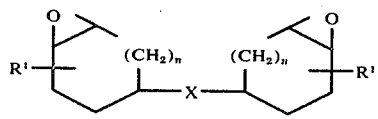

or a bis-epoxide of formula (B)

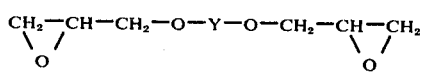

with a hydroxyalkylacrylate or hydroxyalkylmethacrylate containing 2 to 10 carbon atoms in the alkyl portion, $n$ being 0 or 1 in formula (A) with the proviso that if $n$ is 0,
X is —O— and
R¹ is —H; and that if
$n$ is 1,
X is selected from the group of alkylene with 1 to 10 carbon atoms, $C_{1-3}$-alkyl substituted alkylene with 1 to 10 carbon atoms, —O—$(CH_2)_m$—O— where $m$ is 1 to 10, —$CH_2$—OCO—$(CH_2)_p$—COO—$CH_2$ where $p$ is 1 to 6, and —$CH_2$—OCO—, and
R¹ is —H or —$CH_3$, and in formula (B)

Y is

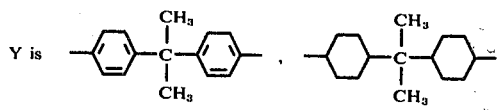

or tricyclo-[5.2.1.0²·⁶]-decylene.

2. Polymerizable diacrylate of claim 1 prepared by the reaction of bis-(2,3-epoxy-cyclopentyl)-ether.

3. Polymerizable diacrylate of claim 1 prepared by the reaction of 2,2-bis(3,4-epoxycyclohexyl)-propane.

4. Polymerizable diacrylate of claim 1 prepared by the reaction of 1,2-bis-(3,4-epoxycyclohexoxy)-ethane.

5. Polymerizable diacrylate of claim 1 prepared by the reaction of bis-(3,4-epoxy-6-methyl-cyclohexylmethyl)-adipate.

6. Polymerizable dimethacrylate of claim 1 prepared by reaction with 2-hydroxyethyl-methacrylate as co-reactant.

7. Polymerizable dimethacrylate of claim 1 prepared by reaction with 2-hydroxypropyl-methacrylate as co-reactant.

8. Polymerizable dimethacrylate of claim 1 prepared by the reaction of 3,4-epoxycyclohexanecarboxylic acid-3',4'-epoxycyclohexylmethylester with 2-hydroxyethylmethacrylate.

* * * * *

UNITED STATES PATENT AND TRADEMARK OFFICE
CERTIFICATE OF CORRECTION

PATENT NO. : 4,002,669
DATED : January 11, 1977
INVENTOR(S) : Albert Gross et al It is certified that error appears in the above—identified patent and that said Letters Patent are hereby corrected as shown below:

Column 3, line 27, "inorganic" should read -- ionogenic --.

Signed and Sealed this

Nineteenth Day of April 1977

[SEAL]

Attest:

RUTH C. MASON
*Attesting Officer*

C. MARSHALL DANN
*Commissioner of Patents and Trademarks*